(12) United States Patent
Brandt et al.

(10) Patent No.: US 10,130,413 B2
(45) Date of Patent: Nov. 20, 2018

(54) TEMPERATURE-SENSING ELECTRICALLY-CONDUCTIVE TISSUE-CONTACTING PLATE AND METHODS OF MANUFACTURING SAME

(71) Applicant: COVIDIEN LP, Mansfield, MA (US)

(72) Inventors: Kim V. Brandt, Loveland, CO (US); Allan G. Aquino, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 889 days.

(21) Appl. No.: 14/538,345

(22) Filed: Nov. 11, 2014

(65) Prior Publication Data

US 2015/0223867 A1   Aug. 13, 2015

Related U.S. Application Data

(60) Provisional application No. 61/938,251, filed on Feb. 11, 2014.

(51) Int. Cl.
*A61B 18/14*   (2006.01)
*A61B 18/12*   (2006.01)
(Continued)

(52) U.S. Cl.
CPC ...... *A61B 18/1445* (2013.01); *A61B 18/1206* (2013.01); *A61B 18/1442* (2013.01);
(Continued)

(58) Field of Classification Search
CPC .................... A61B 2562/12; A61B 18/1445
See application file for complete search history.

(56) References Cited

U.S. PATENT DOCUMENTS 3,343,589 A * 9/1967 Holzl ................ G01K 7/06
                                            136/201
D249,549 S    9/1978 Pike
(Continued)

FOREIGN PATENT DOCUMENTS

CN    201299462       9/2009
DE      2415263 A1   10/1975
(Continued)

OTHER PUBLICATIONS

European Search Report dated Jul. 3, 2015, issued in European Application No. 14200056.1.
(Continued)

*Primary Examiner* — William Levicky

(57) ABSTRACT

An end-effector assembly includes opposing jaw members movably mounted with respect to one another. At least one of the jaw members includes a temperature-sensing electrically-conductive tissue-contacting plate having a tissue-contacting surface and a bottom surface. A first layer is disposed on one or more portions of the bottom surface of the temperature-sensing electrically-conductive tissue-contacting plate. The first layer includes an electrically-insulative material. One or more openings are formed in the first layer. One or more electrically-conductive traces are formed over the electrically-insulative material and associated with the one or more openings. One or more temperature sensors are coupled to the bottom surface of the temperature-sensing electrically-conductive tissue-contacting plate and associated with the one or more openings. The one or more openings are each configured to receive at least a portion of the one or more temperature sensors therein. The one or more temperature sensors are electrically coupled to the one or more electrically-conductive traces.

10 Claims, 9 Drawing Sheets

(51) Int. Cl.
*A61B 17/00* (2006.01)
*A61B 18/00* (2006.01)

(52) U.S. Cl.
CPC ............ *A61B 2017/00526* (2013.01); *A61B 2018/0063* (2013.01); *A61B 2018/00077* (2013.01); *A61B 2018/00083* (2013.01); *A61B 2018/00791* (2013.01); *A61B 2018/00797* (2013.01); *A61B 2018/00815* (2013.01); *A61B 2018/00821* (2013.01); *A61B 2018/1455* (2013.01)

(56) References Cited

U.S. PATENT DOCUMENTS

| | | |
|---|---|---|
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 5,248,311 A * | 9/1993 | Black .................. A61B 18/245 606/11 |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| 5,769,847 A * | 6/1998 | Panescu ................ A61B 18/00 374/E1.005 |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| D670,808 S | 11/2012 | Moua et al. |
| D680,220 S | 4/2013 | Rachlin |
| 2003/0158549 A1 * | 8/2003 | Swanson ............ A61B 18/1445 606/41 |
| 2006/0217709 A1 * | 9/2006 | Couture ............. A61B 18/1442 606/51 |
| 2008/0200969 A1 * | 8/2008 | Weber .................... A61B 18/14 607/102 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202006006759 U1 | 8/2006 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |

(56) References Cited

FOREIGN PATENT DOCUMENTS

| | | | |
|---|---|---|---|
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| JP | 2012239831 A | 12/2012 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A3 | 9/2002 |
| WO | 06/021269 A1 | 3/2006 |
| WO | 05110264 A3 | 4/2006 |
| WO | 08/040483 A1 | 4/2008 |
| WO | 2011/018154 A1 | 2/2011 |
| WO | 2011143468 A2 | 11/2011 |
| WO | 2013030349 A1 | 3/2013 |

OTHER PUBLICATIONS

U.S. Appl. No. 13/731,674, filed Dec. 31, 2012; inventor: Siebrecht.
U.S. Appl. No. 14/065,644, filed Oct. 29, 2013; inventor: Reschke.
U.S. Appl. No. 14/098,953, filed Dec. 6, 2013; inventor: Cunningham.
U.S. Appl. No. 14/100,237, filed Dec. 9, 2013; inventor: Reschke.
U.S. Appl. No. 14/103,971, filed Dec. 12, 2013; inventor: Roy.
U.S. Appl. No. 14/105,374, filed Dec. 13, 2013; inventor: Moua.
U.S. Appl. No. 14/152,618, filed Jan. 10, 2014; inventor: Artale.
U.S. Appl. No. 14/152,690, filed Jan. 10, 2014; inventor: Hart.
U.S. Appl. No. 14/169,358, filed Jan. 31, 2014; inventor: Reschke.
U.S. Appl. No. 14/173,391, filed Feb. 5, 2014; inventor: Kharin.
U.S. Appl. No. 14/176,341, filed Feb. 10, 2014; inventor: Hart.
U.S. Appl. No. 14/177,812, filed Feb. 11, 2014; inventor: Dycus.
U.S. Appl. No. 14/182,894, filed Feb. 18, 2014; inventor: Hart.
U.S. Appl. No. 14/182,967, filed Feb. 18, 2014; inventor: Latimer.
U.S. Appl. No. 14/183,090, filed Feb. 18, 2014; inventor: Arts.
U.S. Appl. No. 14/196,066, filed Mar. 4, 2014; inventor: McCullough.
U.S. Appl. No. 14/250,180, filed Apr. 10, 2014; inventor: Guerra.
U.S. Appl. No. 14/253,017, filed Apr. 15, 2014; inventor: Orszulak.
U.S. Appl. No. 14/260,905, filed Apr. 24, 2014; inventor: Jensen.
U.S. Appl. No. 14/268,051, filed May 2, 2014; inventor: Hart.
U.S. Appl. No. 14/268,140, filed May 2, 2014; inventor: Twomey.
U.S. Appl. No. 14/273,350, filed May 8, 2014; inventor: Gilbert.
U.S. Appl. No. 14/274,445, filed May 9, 2014; inventor: Hixson.
U.S. Appl. No. 14/276,465, filed May 13, 2014; inventor: Kappus.
U.S. Appl. No. 14/282,738, filed May 20, 2014; inventor: Rachlin.
U.S. Appl. No. 14/284,618, filed May 22, 2014; inventor: Hempstead.
U.S. Appl. No. 14/286,105, filed May 23, 2014; inventor: Johnson.
U.S. Appl. No. 14/294,316, filed Jun. 3, 2014; inventor: Johnson.
U.S. Appl. No. 14/295,049, filed Jun. 3, 2014; inventor: Couture.
U.S. Appl. No. 14/295,730, filed Jun. 4, 2014; inventor: Sartor.
U.S. Appl. No. 14/295,757, filed Jun. 4, 2014; inventor: McKenna.
U.S. Appl. No. 14/297,316, filed Jun. 5, 2014; inventor: Ackley.
U.S. Appl. No. 14/297,404, filed Jun. 5, 2014; inventor: Allen.
U.S. Appl. No. 14/299,740, filed Jun. 9, 2014; inventor: Larson.
U.S. Appl. No. 14/319,869, filed Jun. 30, 2014; inventor: Cunningham.
U.S. Appl. No. 14/322,513, filed Jul. 2, 2014; inventor: Duffin.
U.S. Appl. No. 14/335,303, filed Jul. 18, 2014; inventor: Lee.

Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With The LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.

(56) References Cited

OTHER PUBLICATIONS

Levy et al. "Randomized Trial of Suture Versus Electrosurgical Bipolar Vessel Sealing in Vaginal hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C . . . .
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C . . . .
McLellan et al. "Vessel Sealing for Hemostasis During Gynecologic Surgery" Sales/Product Literature 1999.
U.S. Appl. No. 08/926,869, filed Sep. 10, 1997; inventor: James G. Chandler.
U.S. Appl. No. 09/177,950, filed Oct. 23, 1998; inventor: Randel A. Frazier.
U.S. Appl. No. 09/387,883, filed Sep. 1, 1999; inventor: Dale F. Schmaltz.
U.S. Appl. No. 09/591,328, filed Jun. 9, 2000; inventor: Thomas P. Ryan.
U.S. Appl. No. 12/336,970, filed Dec. 17, 2008; inventor: Paul R. Sremcich.

* cited by examiner

TEMPERATURE-SENSING ELECTRICALLY-CONDUCTIVE TISSUE-CONTACTING PLATE AND METHODS OF MANUFACTURING SAME

CROSS REFERENCE TO RELATED APPLICATION

The present application claims the benefit of and priority to U.S. Provisional Application Ser. No. 61/938,251, filed on Feb. 11, 2014, the entire contents of which are incorporated herein by reference.

BACKGROUND

1. Technical Field

The present disclosure relates to electrosurgical instruments. More particularly, the present disclosure relates to temperature-sensing electrically-conductive tissue-contacting plates configured for use in electrosurgical jaw members and methods of manufacturing the same.

2. Discussion of Related Art

Electrosurgical instruments, such as electrosurgical forceps, are well known in the medical arts. Electrosurgery involves the application of thermal and/or electrical energy to cut, dissect, ablate, coagulate, cauterize, seal or otherwise treat biological tissue during a surgical procedure. Electrosurgery is typically performed using an electrosurgical generator operable to output energy and a handpiece including a surgical instrument (e.g., end effector) adapted to transmit energy to a tissue site during electrosurgical procedures. Electrosurgery is typically performed using either a monopolar or a bipolar instrument.

The basic purpose of both monopolar and bipolar electrosurgery is to produce heat to achieve the desired tissue/clinical effect. In monopolar electrosurgery, devices use an instrument with a single, active electrode to deliver energy from an electrosurgical generator to tissue, and a patient return electrode or pad that is attached externally to the patient (e.g., a plate positioned on the patient's thigh or back) as the means to complete the electrical circuit between the electrosurgical generator and the patient. When the electrosurgical energy is applied, the energy travels from the active electrode, to the surgical site, through the patient and to the return electrode.

In bipolar electrosurgery, both the active electrode and return electrode functions are performed at the site of surgery. Bipolar electrosurgical devices include two electrodes that are located in proximity to one another for the application of current between their respective surfaces. Bipolar electrosurgical current travels from one electrode, through the intervening tissue to the other electrode to complete the electrical circuit. Bipolar instruments generally include end-effectors, such as graspers, cutters, forceps, dissectors and the like.

Bipolar electrosurgical forceps utilize two generally opposing electrodes that are operably associated with the inner opposing surfaces of the end effectors and that are both electrically coupled to an electrosurgical generator. In bipolar forceps, the end-effector assembly generally includes opposing jaw members pivotably mounted with respect to one another. In a bipolar configuration, only the tissue grasped between the jaw members is included in the electrical circuit. Because the return function is performed by one jaw member of the forceps, no patient return electrode is needed.

A variety of types of end-effector assemblies have been employed for various types of electrosurgery using a variety of types of monopolar and bipolar electrosurgical instruments. Jaw member components of end-effector assemblies for use in electrosurgical instruments are required to meet specific tolerance requirements for proper jaw alignment and other closely-toleranced features. Gap tolerances and/or surface parallelism and flatness tolerances are parameters that, if properly controlled, can contribute to a consistent and effective tissue seal. Thermal resistance, strength and rigidity of surgical jaw members also play a role in determining the reliability and effectiveness of electrosurgical instruments.

By utilizing an electrosurgical forceps, a surgeon can cauterize, coagulate, desiccate and/or seal tissue and/or simply reduce or slow bleeding by controlling the intensity, frequency and duration of the electrosurgical energy applied through the jaw members to the tissue. During the sealing process, mechanical factors such as the pressure applied to the vessel or tissue between opposing jaw members and the gap distance between the electrically-conductive tissue-contacting surfaces (electrodes) of the jaw members play a role in determining the resulting thickness of the sealed tissue and effectiveness of the seal. Accurate application of pressure is important to oppose the walls of the vessel; to reduce the tissue impedance to a low enough value that allows enough electrosurgical energy through the tissue; to overcome the forces of expansion during tissue heating; and to contribute to the end tissue thickness which is an indication of a good seal. A variety of instruments have been developed that utilize technology to form a vessel seal utilizing a combination of pressure, gap distance between opposing surfaces and electrical control to effectively seal tissue or vessels.

Methods and systems have been developed for controlling an output of a generator, such as a radio-frequency (RF) electrosurgical generator, based on sensor signals indicative of impedance changes at a surgical site. In some systems employing changes in impedance to control the amount of electrosurgical energy applied to tissue, when the sensor signal meets a predetermined level based on a control algorithm, the system provides an end tone that indicates to the surgeon that a procedure, such as a vessel-sealing procedure, is complete. In generators employing an impedance-based control algorithm, impedance is a proxy for temperature, and there are cases where an end tone may be given when no tissue sealing has occurred because the impedance proxy was incorrect.

SUMMARY

A continuing need exists for temperature-sensing devices that can be readily integrated into the manufacturing process for electrosurgical jaw members. A need exists for the development of a manufacturing process that effectively fabricates temperature-sensing electrically-conductive tissue-contacting plates configured for use in electrosurgical jaw members and results in the formation of a reliable instrument that meets specific tolerance requirements for proper jaw alignment and/or gap distances. Further need exists for the development of a manufacturing process that effectively fabricates temperature-sensing electrically-conductive tissue-contacting plates including a configuration of temperature sensors disposed on a bottom surface thereof.

According to an aspect of the present disclosure, an end-effector assembly is provided. The end-effector assembly includes opposing jaw members movably mounted with respect to one another. At least one of the jaw members includes a temperature-sensing electrically-conductive tissue-contacting plate having a tissue-contacting surface and a bottom surface. A first layer is disposed on one or more portions of the bottom surface of the temperature-sensing electrically-conductive tissue-contacting plate. The first layer includes an electrically-insulative material. One or more openings are formed in the first layer. One or more electrically-conductive traces are formed over the electrically-insulative material and associated with the one or more openings. One or more temperature sensors are coupled to the bottom surface of the temperature-sensing electrically-conductive tissue-contacting plate and associated with the one or more openings. The one or more openings are each configured to receive at least a portion of the one or more temperature sensors therein. The one or more temperature sensors are electrically coupled to the one or more electrically-conductive traces.

According to another aspect of the present disclosure, a method of manufacturing a jaw member suitable for use in an electrosurgical end-effector assembly is provided. The method includes the initial step of providing temperature-sensing electrically-conductive tissue-contacting plate having a bottom surface. The structural support member is configured to mechanically engage the bottom surface. The method also includes the steps of applying a first layer formed of an electrically-insulative material to the bottom surface and forming one or more openings in the first layer. Each one of the one or more openings is configured to receive at least a portion of a temperature sensor therein. The method also includes the steps of forming one or more electrically-conductive traces on the first layer and coupling one or more temperature sensors to the bottom surface. Each one of the one or more electrically-conductive traces is associated with a different one of the one or more openings. Each one of the one or more temperature sensors is associated with a different one of the one or more openings and operably coupled to a different one of the one or more electrically-conductive traces.

According to another aspect of the present disclosure, a method of manufacturing a temperature-sensing electrically-conductive tissue-contacting plate suitable for use in an electrosurgical jaw member is provided including the initial steps of providing an electrically-conductive substrate having a bottom surface and applying a first layer to the bottom surface of the electrically-conductive substrate. The first layer includes an electrically-conductive material formed over one or more portions of an electrically-insulative material. The method also includes the steps of forming one or more openings in the first layer and etching portions of the electrically-conductive material from the first layer to form one or more electrically-conductive traces. Each one of the one or more openings is configured to receive at least a portion of a temperature sensor therein. Each one of the one or more electrically-conductive traces is associated with a different one of the one or more openings. The method also includes the step of coupling one or more temperature sensors to the bottom surface of the electrically-conductive substrate. Each one of the one or more temperature sensors is associated with a different one of the one or more openings.

BRIEF DESCRIPTION OF THE DRAWINGS

Objects and features of the presently-disclosed temperature-sensing electrically-conductive tissue-contacting plates configured for use in electrosurgical jaw members and methods of manufacturing the same will become apparent to those of ordinary skill in the art when descriptions of various embodiments thereof are read with reference to the accompanying drawings, of which.

DETAILED DESCRIPTION

Figure 1:
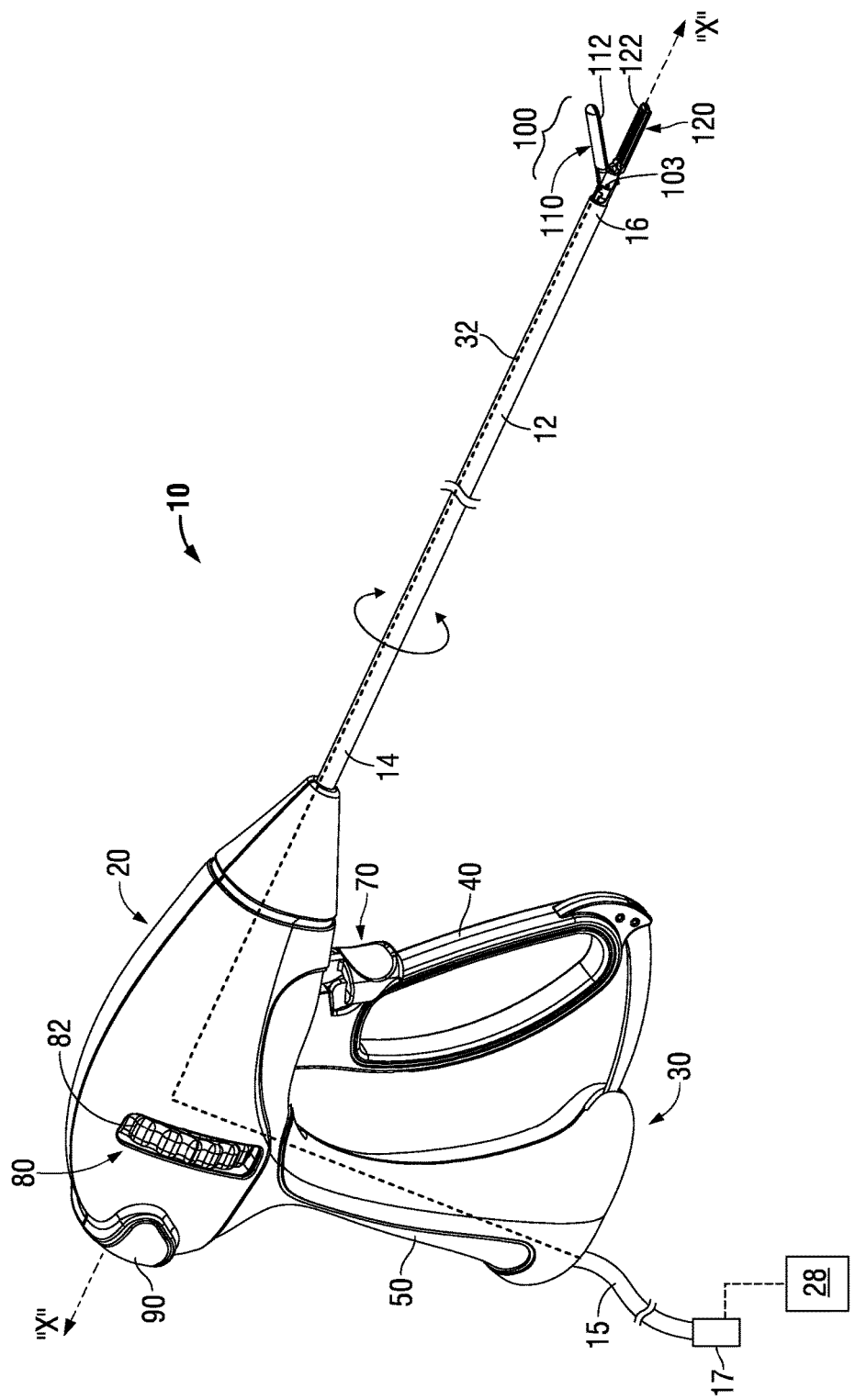
FIG. 1 is a left, perspective view of an endoscopic bipolar forceps showing a housing, a rotatable member, a shaft, and an end-effector assembly having first and second jaw members including temperature-sensing electrically-conductive tissue-contacting plates in accordance with an embodiment of the present disclosure.

Hereinafter, embodiments of a temperature-sensing electrically-conductive tissue-contacting plate configured for use in an electrosurgical jaw member and methods of manufacturing the same of the present disclosure are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure.

As it is used in this description, "electrically-conductive tissue-contacting plate" generally refers to an electrically-conductive member including one or more tissue engaging surfaces that can be used to transfer energy from an electrosurgical power generating source, such as RF electrosurgical generator, to tissue. As it is used in this description, "electrically conductive", or simply "conductive", generally refers to materials that are capable of electrical conductivity, including, without limitation, materials that are highly conductive, e.g., metals and alloys, or materials that are semi-conductive, e.g., semi-conducting materials and composites. As it is used in this description, "transmission line" generally refers to any transmission medium that can be used for the propagation of signals from one point to another.

Vessel sealing or tissue sealing utilizes a combination of radiofrequency energy, pressure and gap control to effectively seal or fuse tissue between two opposing jaw members or sealing plates thereof. Vessel or tissue sealing is more than "cauterization" which may be defined as the use of heat to destroy tissue (also called "diathermy" or "electrodiathermy"), and vessel sealing is more than "coagulation" which may be defined as a process of desiccating tissue wherein the tissue cells are ruptured and dried. As it is used in this description, "vessel sealing" generally refers to the process of liquefying the collagen, elastin and ground substances in the tissue so that it reforms into a fused mass with significantly-reduced demarcation between the opposing tissue structures.

Various embodiments of the present disclosure provide electrosurgical instruments suitable for sealing, cauterizing, coagulating, desiccating, and/or cutting tissue, e.g., vessels and vascular tissue, during a surgical procedure. Embodiments of the presently-disclosed electrosurgical instruments may be suitable for utilization in endoscopic surgical procedures and/or suitable for utilization in open surgical applications. Embodiments of the presently-disclosed electrosurgical instruments may be implemented using electrosurgical energy at radio frequencies (RF) and/or at other frequencies.

Various embodiments of the present disclosure provide electrosurgical instruments that include an end-effector assembly having jaw members including a temperature-sensing electrically-conductive tissue-contacting plate including one or more temperature sensors coupled to a bottom surface thereof. One or more operating parameters of an electrosurgical power generating source may be controlled based on one or more signals indicative of a temperature sensed by the one or more temperature sensors coupled to the bottom surface of each one of the temperature-sensing electrically-conductive tissue-contacting plates. The presently-disclosed tissue-contacting plate embodiments may include a plurality of zones, wherein each zone includes one or more temperature sensors (and/or pressure sensors), e.g., to provide feedback to an electrosurgical power generating source configured to turn on/off different zones to provide more uniform heating patterns across the jaw members and/or to help control thermal spread.

The various embodiments disclosed herein may also be configured to work with robotic surgical systems and what is commonly referred to as "Telesurgery." Such systems employ various robotic elements to assist the surgeon in the operating theater and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include, remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely controls the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. In various embodiments disclosed herein, an end-effector assembly may be coupled to a pair of master handles by a controller. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the jaw members onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Although the following description describes the use of an endoscopic bipolar forceps, the teachings of the present disclosure may also apply to a variety of electrosurgical devices that include an end-effector assembly.

In FIG. 1, an embodiment of an electrosurgical instrument 10, e.g., an endoscopic bipolar forceps, is shown for use with various surgical procedures and generally includes a housing 20, a handle assembly 30, a rotatable assembly 80, a trigger assembly 70 and an end-effector assembly 100 that mutually cooperate to grasp, seal and/or divide tubular vessels and vascular tissue (not shown). Handle assembly 30 includes a fixed handle 50 and a movable handle 40. Although FIG. 1 depicts a bipolar forceps 10 for use in connection with endoscopic surgical procedures, the teachings of the present disclosure may also apply to more traditional open surgical procedures. For the purposes herein, the device 10 is described in terms of an endoscopic instrument; however, it is contemplated that an open version of a forceps may also include the same or similar operating components and features as described below.

As shown in FIG. 1, the shaft 12 includes a distal end 16 configured to mechanically engage the end-effector assembly 100. In some embodiments, the end-effector assembly 100 is selectively and releaseably engageable with the distal end 16 of the shaft 12. The proximal end 14 of the shaft 12 is received within the housing 20, and connections relating thereto are shown and described in commonly assigned U.S. Pat. No. 7,150,097 entitled "METHOD OF MANUFACTURING JAW ASSEMBLY FOR VESSEL SEALER AND DIVIDER," commonly assigned U.S. Pat. No. 7,156,846 entitled "VESSEL SEALER AND DIVIDER FOR USE WITH SMALL TROCARS AND CANNULAS," commonly assigned U.S. Pat. No. 7,597,693 entitled "VESSEL SEALER AND DIVIDER FOR USE WITH SMALL TROCARS AND CANNULAS," and commonly assigned U.S. Pat. No. 7,771,425 entitled "VESSEL SEALER AND DIVIDER HAVING A VARIABLE JAW CLAMPING MECHANISM."

End-effector assembly 100 generally includes a pair of opposing jaw members 110 and 120 movably mounted with respect to one another. End-effector assembly 100 is configured as a unilateral assembly, i.e., the end-effector assembly 100 includes a stationary or fixed jaw member 120 mounted in fixed relation to the shaft 12 and a pivoting jaw member 110 mounted about a pivot pin 103 coupled to the stationary jaw member 120. Alternatively, the forceps 10 may include a bilateral jaw assembly, i.e., both jaw members move relative to one another.

Figure 2:
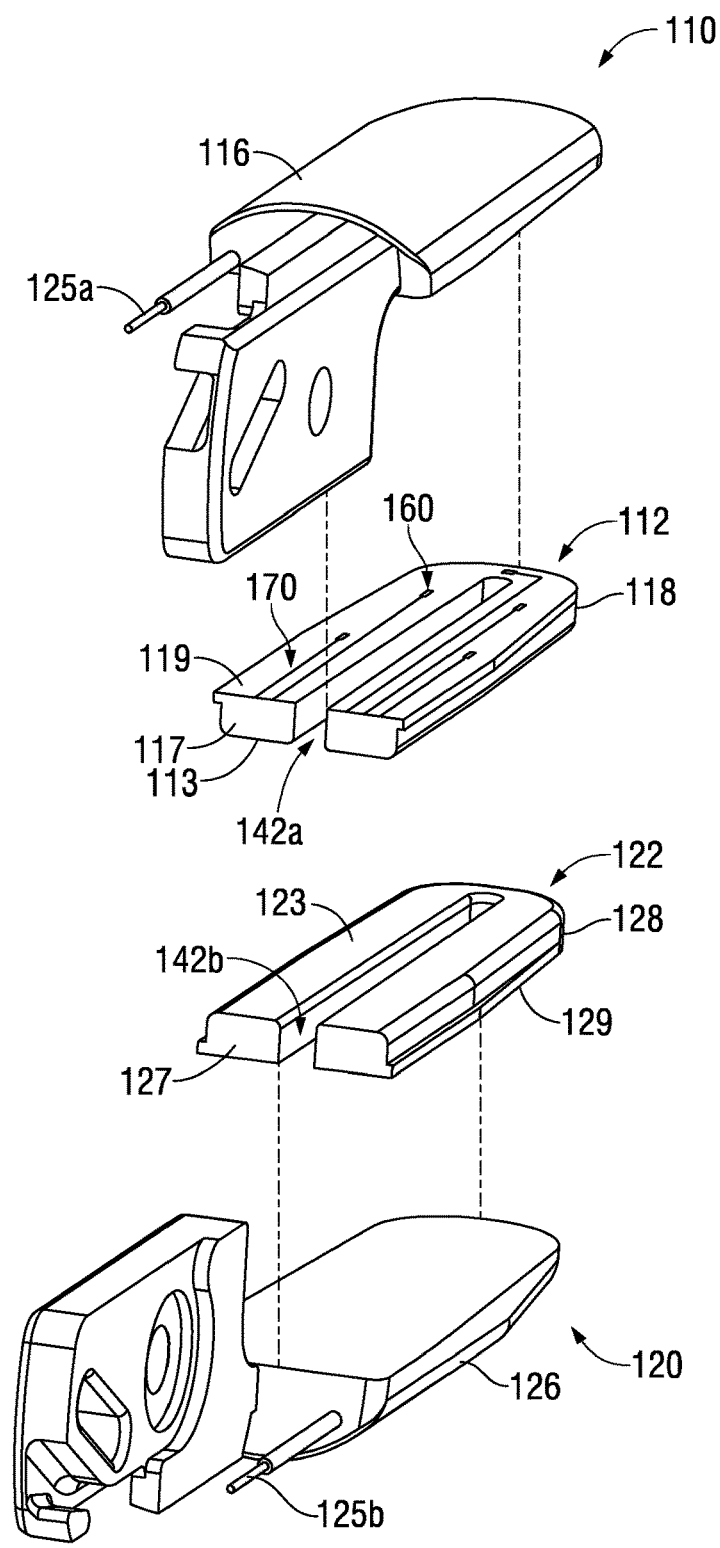
FIG. 2 is an enlarged, perspective view of the first and second jaw members of the end-effector assembly of FIG. 1, shown with parts separated, illustrating a first configuration of a sensor arrangement associated with the temperature-sensing electrically-conductive tissue-contacting plate of the first jaw member in accordance with an embodiment of the present disclosure.

As shown in FIG. 2, the jaw members 110 and 120 include a structural support member 116 and 126, respectively, and a temperature-sensing electrically-conductive tissue-contacting plate 112 and 122, respectively. Temperature-sensing electrically-conductive tissue-contacting plate 112 includes a tissue-contacting surface 113, a bottom surface 119, and a slot 142a defined therethrough. Temperature-sensing electrically-conductive tissue-contacting plate 122 includes a tissue-contacting surface 123, a bottom surface 129, and a slot 142b defined therethrough.

The structural support members 116 and 126 are configured to mechanically engage the bottom surfaces 119 and 129, respectively. Structural support members 116 and 126 may be manufactured from any suitable materials, e.g., metal, plastic and the like.

Slots 142a and 142b extend distally from a proximal end 117 and 127, respectively, of the temperature-sensing electrically-conductive tissue-contacting plates 112 and 122 and provide a path for longitudinal translation of a knife blade (not shown) therein. In some embodiments, the temperature-sensing electrically-conductive tissue-contacting plates 112 and 122 are configured in such a manner that when the jaw members 110 and 120 are in a closed configuration, a knife blade (not shown), or portion thereof, is translatable within a knife channel formed by the slot 142a of temperature-sensing electrically-conductive tissue-contacting plate 112 and the slot 142b of temperature-sensing electrically-conductive tissue-contacting plate 122.

Figure 3:
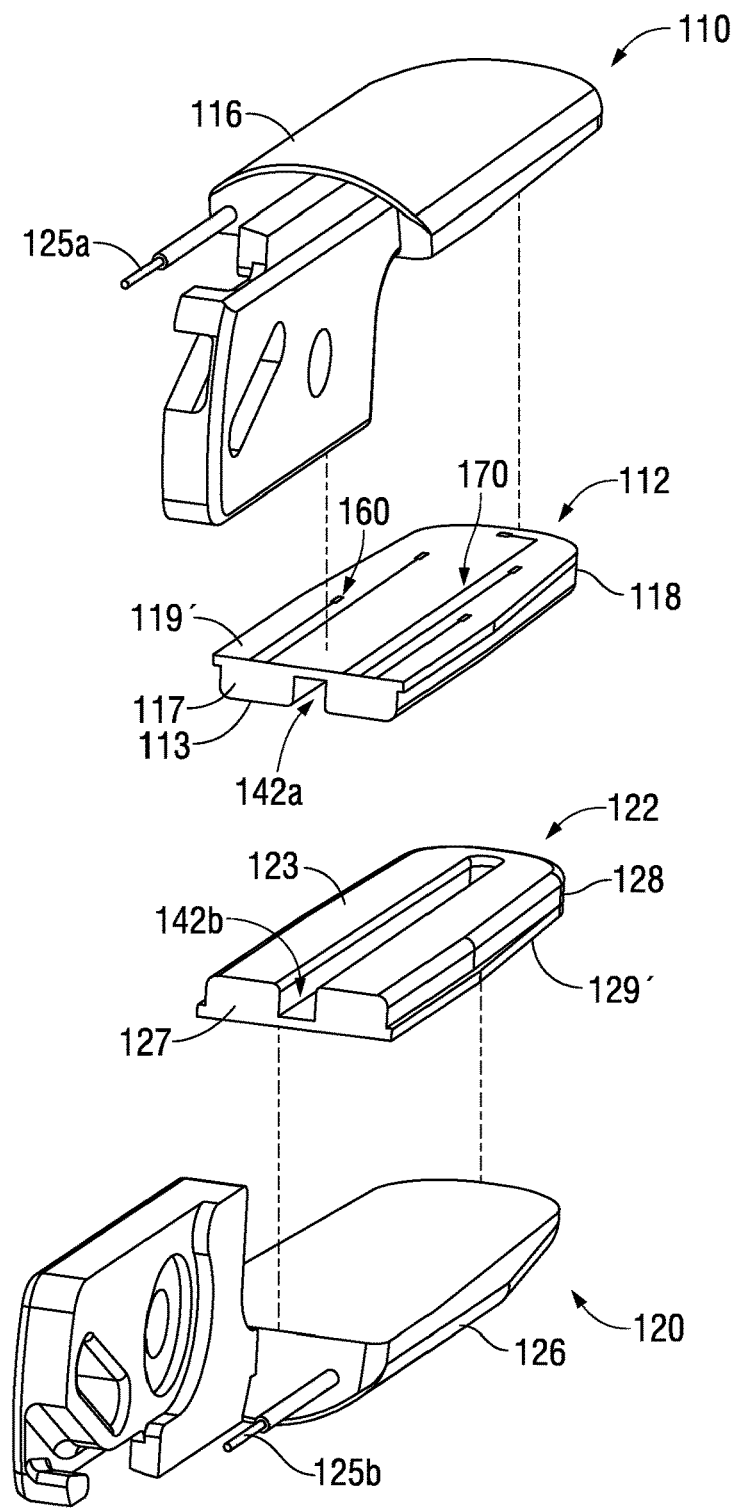
FIG. 3 is an enlarged, perspective view of the first and second jaw members of FIG. 2, shown with parts separated, illustrating an alternative embodiment of the bottom surface of the temperature-sensing electrically-conductive tissue-contacting plates in accordance with the present disclosure.

In some embodiments, as shown in FIG. 2, slots 142a and 142b are open at the bottom surface 119 and 129 of their respective temperature-sensing electrically-conductive tissue-contacting plates 112 and 122. In some embodiments, as shown in FIG. 3, slots 142a and 142b are closed at the bottom surface 119' and 129' of their respective temperature-sensing electrically-conductive tissue-contacting plates 112 and 122.

In some embodiments, the temperature-sensing electrically-conductive tissue-contacting plates 112 and 122 may have a thickness that varies (i.e., non-uniform) from a proximal end 117 and 127 to a distal end 118 and 128, respectively. For example, temperature-sensing electrically-conductive tissue-contacting plates 112 and 122 each may have a proximal end 117 and 127, respectively, having a thickness that is slightly larger than a thickness at the distal end 118 and 128 thereof, e.g., depending on a particular purpose.

Jaw members 110 and 120 are electrically isolated from one another. End-effector assembly 100 (FIG. 1) may additionally, or alternatively, include electrically-insulative members and/or electrically-insulative, thermally non-degrading coatings configured to electrically isolate, at least in part, the temperature-sensing electrically-conductive tissue-contacting plates 112 and 122 from the jaw members 110 and 120, respectively.

As shown in FIG. 1, the end-effector assembly 100 is rotatable about a longitudinal axis "X-X" defined through shaft 12, either manually or otherwise, by the rotatable assembly 80. Rotatable assembly 80 generally includes two halves (not shown), which when assembled form a generally circular rotatable member 82. Rotatable assembly 80, or portions thereof, may be configured to house a drive assembly (not shown) and/or a knife assembly (not shown), or components thereof. Examples of rotatable assembly embodiments, drive assembly embodiments, knife assembly embodiments, and handle assembly embodiments of the electrosurgical instrument 10 are shown and described in the above-mentioned, commonly-assigned U.S. Pat. Nos. 7,150,097, 7,156,846, 7,597,693 and 7,771,425.

Electrosurgical instrument 10 includes a switch 90 configured to permit the user to selectively activate the instrument 10 in a variety of different orientations, i.e., multi-oriented activation. When the switch 90 is depressed, electrosurgical energy is transferred through one or more electrical leads (e.g., leads 125a and 125b shown in FIGS. 2 and 3) to the jaw members 110 and 120.

Forceps 10 includes an electrosurgical cable 15 formed from a suitable flexible, semi-rigid or rigid cable, and may connect directly to an electrosurgical power generating source 28, e.g., a microwave or RF electrosurgical generator. In some embodiments, the electrosurgical cable 15 connects the forceps 10 to a connector 17, which further operably connects the instrument 10 to the electrosurgical power generating source 28.

Electrosurgical power generating source 28 may be any generator suitable for use with electrosurgical devices, and may be configured to provide various frequencies of electromagnetic energy. Examples of electrosurgical generators that may be suitable for use as a source of electrosurgical energy are commercially available under the trademarks FORCE EZ™, FORCE FX™, SURGISTAT™ II, and FORCE TRIAD™ offered by Covidien. Forceps 10 may alternatively be configured as a wireless device or battery-powered.

Figure 4:
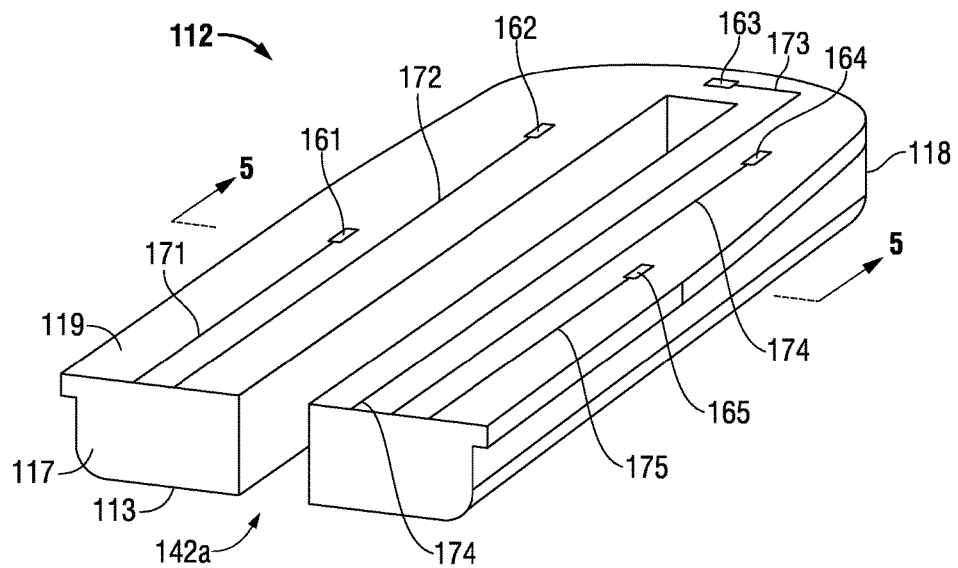
FIG. 4 is an enlarged, perspective view of the temperature-sensing electrically-conductive tissue-contacting plate of the first jaw member shown in FIG. 2.
Figure 5:
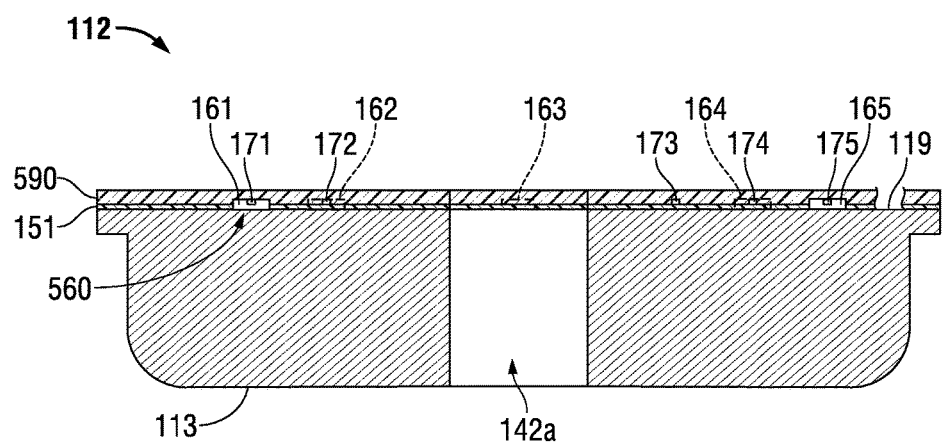
FIG. 5 is a cross-sectional view taken along the lines "5-5" of FIG. 4 illustrating a first configuration of a sensor arrangement associated with the temperature-sensing electrically-conductive tissue-contacting plate of the first jaw member in accordance with an embodiment of the present disclosure.

As shown in FIGS. 2 and 4, the temperature-sensing electrically-conductive tissue-contacting plate 112 of the first jaw member 110 includes a configuration of a plurality of sensors located on the bottom surface 119 thereof. As seen in FIG. 4, the temperature-sensing electrically-conductive tissue-contacting plate 112 includes a first sensor 161, a second sensor 162, a third sensor 163, a fourth sensor 164, and a fifth sensor 165 disposed on the bottom surface 119. The first and second sensors 161 and 162 are disposed in spaced relation relative to one another on the bottom surface 119 along one side of the slot 142a, and the fourth and fifth sensors 164 and 165 are disposed in spaced relation relative to one another on the bottom surface 119 along the opposite side of the slot 142a. The third sensor 163 is disposed on the bottom surface 119 proximate the distal end 118 of the temperature-sensing electrically-conductive tissue-contacting plate 112.

In some embodiments, the first, second, third, fourth and fifth sensors 161, 162, 163, 164 and 165, respectively, are temperature sensors, e.g., thermocouples and/or thermistors. One or more of the sensors 161-165 may be a thermocouple that includes one or more deposited layers formed utilizing vapor deposition. Additionally, or alternatively, one or more of the first, second, third, fourth and fifth sensors 161, 162, 163, 164 and 165, respectively, may be J-type thermocouples; however, it is to be understood that any suitable type of thermocouple may be utilized.

In some embodiments, the first, second, third, fourth and fifth sensors 161, 162, 163, 164 and 165, respectively, are electrically coupled to first, second, third, fourth and fifth electrically-conductive traces 171, 172, 173, 174 and 175, respectively. A variety of trace geometries may be used, e.g., planar conductor lines.

Electrically-conductive traces 171-175 may be formed by a subtractive process, e.g., an etching process, to selectively remove the conductor where it is not needed to form lines. For example, planar conductor lines may be formed by chemically etching away unwanted areas of material, e.g., metal, from a conductor layer, such as copper. Some methods for etching through a conductor layer involve placing a photoresist on the surface of the conductor layer, exposing the photoresist to a particular wavelength of light, developing the photoresist to form a mask which exposes the conductor layer where it is to be removed, and removing the exposed conductor layer with either a wet or a dry etchant. In other embodiments, electrically-conductive traces 171-175 may formed using an additive process, e.g., sputtering, where atoms of the conductor are knocked from a target made of the conductor and splattered onto the surface of the insulative-material layer, or vapor deposition, where the conductor is carried to the insulative-material layer in a vapor state and condenses on the surface of the insulative-material layer.

Figure 6:
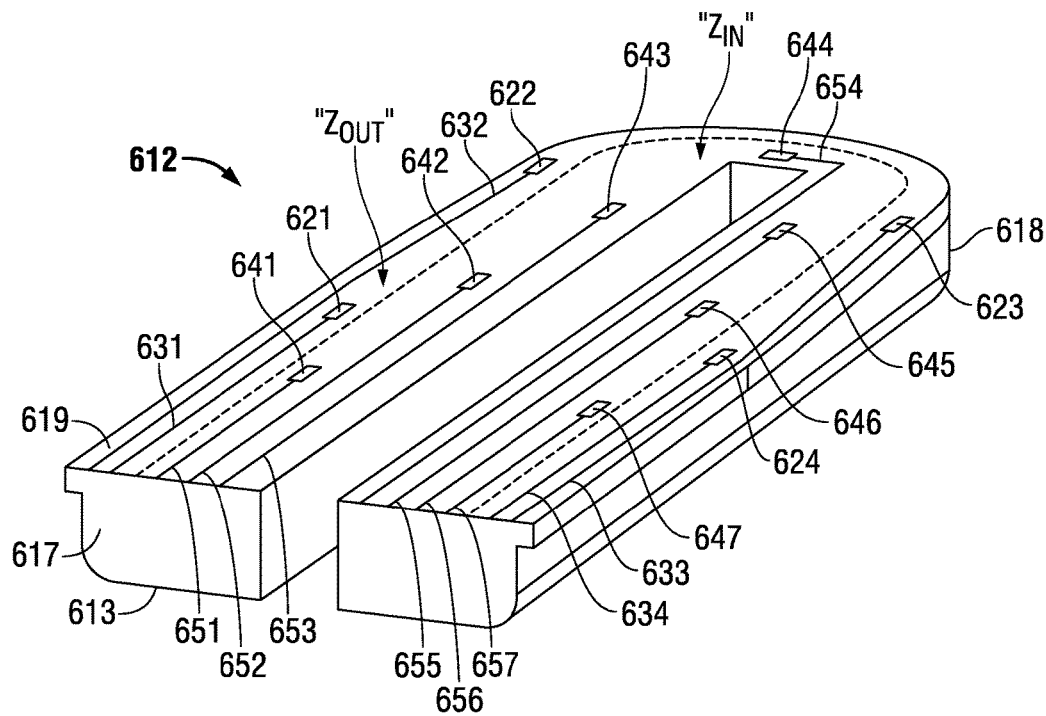
FIG. 6 is an enlarged, perspective view of a temperature-sensing electrically-conductive tissue-contacting plate illustrating a second configuration of a sensor arrangement in accordance with an embodiment of the present disclosure.

FIG. 6 shows a temperature-sensing electrically-conductive tissue-contacting plate 612 that includes a tissue-contacting surface 613 and a bottom surface 619. The tissue-contacting surface 613 may be curved or straight depending upon a particular surgical purpose. For example, the tissue-contacting surface 613 may be curved at various angles to facilitate manipulation of tissue and/or to provide enhanced line-of-sight for accessing targeted tissues. In some embodiments, the temperature-sensing electrically-conductive tissue-contacting plate 612 may have a thickness that varies (i.e., non-uniform) from a proximal end 617 to a distal end 618 thereof.

Temperature-sensing electrically-conductive tissue-contacting plate 612 includes a plurality of sensors associated with the bottom surface 619 thereof. As seen FIG. 6, bottom surface 619 is arranged into two different regions or zones, as indicated by the generally U-shaped dashed line in FIG. 6. For ease of understanding, the region around the periphery of the bottom surface 119 disposed outwardly of the dashed line in FIG. 6 is referred to herein as the outer zone "$Z_{OUT}$", and the region disposed inwardly of the dashed line in FIG. 6 is referred to herein as the inner zone "$Z_{IN}$".

One or more sensors, e.g., temperature sensors, may be disposed within the outer zone "$Z_{OUT}$" and/or one or more sensors, e.g., temperature sensors, may be disposed within the inner zone "$Z_{IN}$". In some embodiments, as shown in FIG. 6, a first sensor 621, a second sensor 622, a third sensor 623 and a fourth sensor 624 are disposed within the outer zone "$Z_{OUT}$", and a first sensor 641, a second sensor 642, a third sensor 643, a fourth sensor 644, a fifth sensor 645, a sixth sensor 646 and a seventh sensor 647 are disposed within the inner zone "$Z_{IN}$". The first, second, third and fourth sensors 621, 622, 623 and 624, respectively, are electrically coupled to first, second, third and fourth electrically-conductive traces 631, 632, 633 and 634, respectively. The first, second, third, fourth, fifth, sixth and seventh sensors 641, 642, 643, 644, 645, 646 and 647, respectively, are electrically coupled to first, second, third, fourth, fifth, sixth and seventh electrically-conductive traces 651, 652, 653, 654, 655, 656 and 657, respectively.

In some embodiments, the sensors 621-624 and/or the sensors 641-647 include thermocouples and/or thermistors. In some embodiments, the sensors 621-624 and/or the sensors 641-647 may include J-type thermocouples, but it is to be understood that any suitable type of thermocouple may be utilized. In alternative embodiments, one or more of the sensors 621-624 and/or one or more of the sensors 641-647 may include pressure sensors (e.g., piezo sensors, multilayer bending sensors, etc.).

Figure 7:
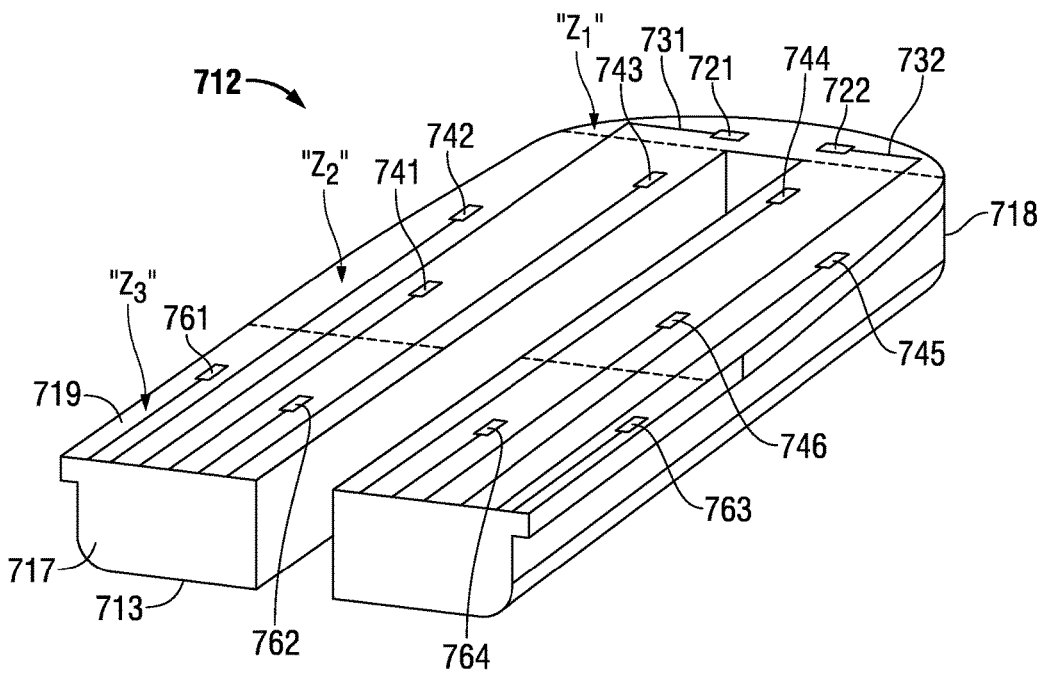
FIG. 7 is an enlarged, perspective view of a temperature-sensing electrically-conductive tissue-contacting plate illustrating a third configuration of a sensor arrangement in accordance with an embodiment of the present disclosure.

FIG. 7 shows a temperature-sensing electrically-conductive tissue-contacting plate 712 having a proximal end 717, a distal end 718, a tissue-contacting surface 713, and a bottom surface 719. Temperature-sensing electrically-conductive tissue-contacting plate 712 includes a plurality of sensors associated with the bottom surface 719 thereof. As seen FIG. 7, bottom surface 619 includes three different regions or zones, as indicated by the dashed lines in FIG. 7. The region at a distal end portion of the bottom surface 119 is referred to herein as the first zone "$Z_1$", the middle region is referred to herein as the second zone "$Z_2$", and the region at a proximal end portion or "heel" of the temperature-sensing electrically-conductive tissue-contacting plate 712 is referred to herein as the third zone "$Z_3$".

In some embodiments, as shown in FIG. 7, two sensors (e.g., a first sensor 721 and a second sensor 722) are disposed within the first zone "$Z_1$", six sensors (e.g., a first sensor 741, a second sensor 742, a third sensor 743, a fourth sensor 744, a fifth sensor 745 and a sixth sensor 746) are disposed within the second zone "$Z_2$", and fours sensors (e.g., a first sensor 761, a second sensor 762, a third sensor 763 and a fourth sensor 764) are disposed within the third zone "$Z_3$". As seen in FIG. 7, a plurality of electrically-conductive traces is provided. For example, the first and second sensors 721 and 722, respectively, are electrically coupled to first and second electrically-conductive traces 731 and 732, respectively.

In some embodiments, the sensors 721-722, the sensors 741-746, and/or the sensors 761-764 may include temperature sensors (e.g., thermocouples, thermistors, etc.) and/or pressure sensors (e.g., piezo sensors, multilayer bending sensors, etc.).

Figure 8:
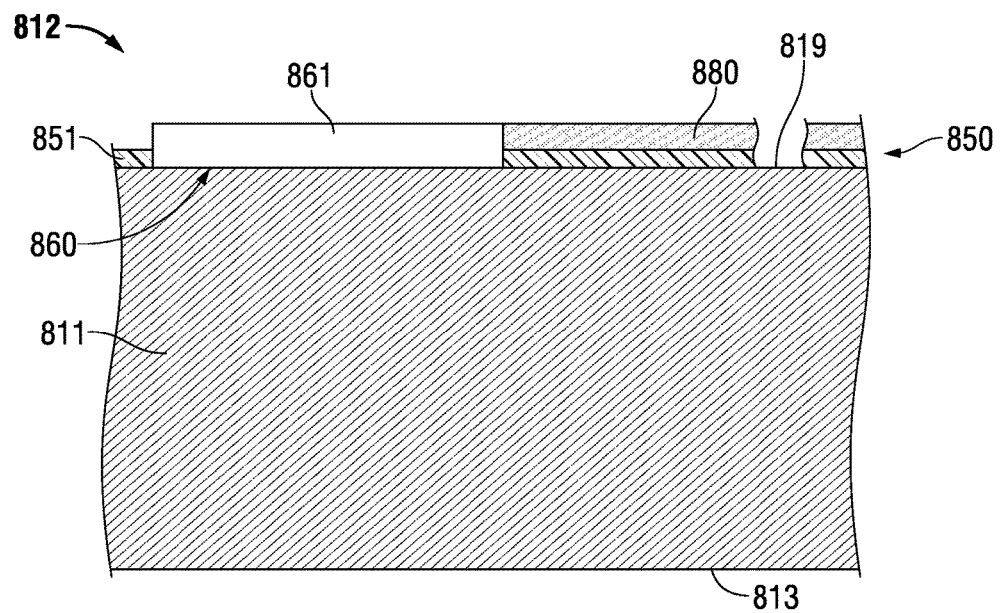
FIG. 8 is an enlarged, cross-sectional view of a portion of a temperature-sensing electrically-conductive tissue-contacting plate having a bottom surface including a temperature sensor coupled thereto, a first electrically-insulative material layer disposed on a portion of the bottom surface, and an electrically-conductive trace disposed on a portion of the first electrically-insulative material layer in accordance with an embodiment of the present disclosure.

In FIG. 8, a portion of a temperature-sensing electrically-conductive tissue-contacting plate 812 is shown in cross-section and includes a tissue-contacting surface 813. FIG. 8 shows a first layer 850 formed of an electrically-insulative material 851 disposed on a portion of the bottom surface 819 of an electrically-conductive substrate 811. An electrically-conductive trace 880 is disposed on a portion of the first layer 850. Formed in the first layer 850 is an opening 860 configured to receive at least a portion of a temperature sensor 861 therein.

Figure 9:
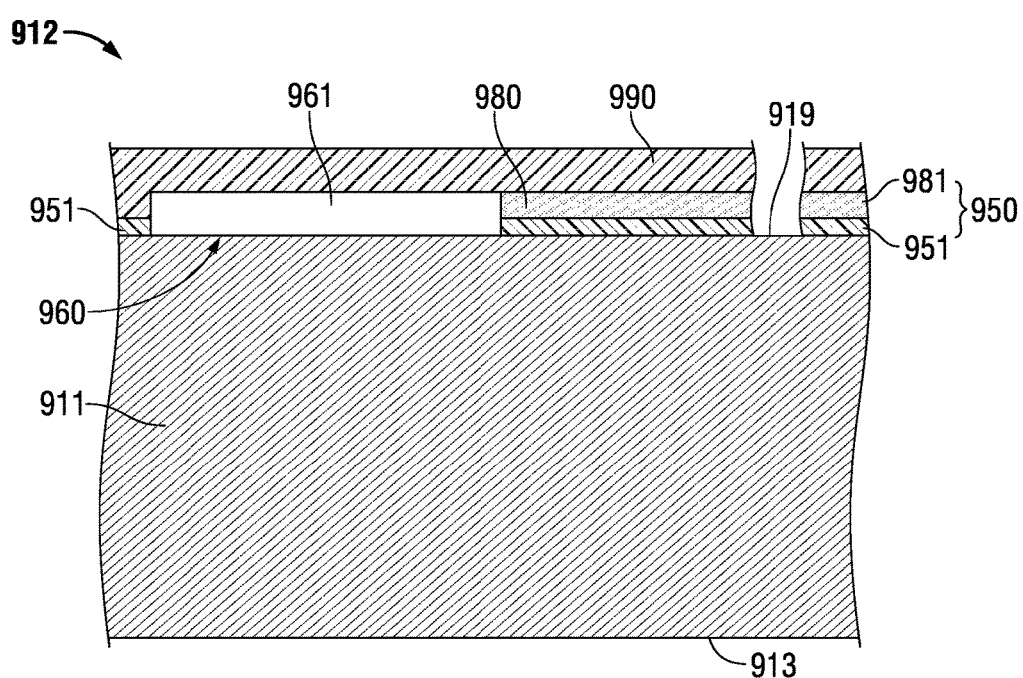
FIG. 9 is an enlarged, cross-sectional view of a temperature-sensing electrically-conductive tissue-contacting plate including a second electrically-insulative material layer covering a temperature sensor, an electrically-conductive trace, and a first electrically-insulative material layer in accordance with an embodiment of the present disclosure.

In FIG. 9, a portion of a temperature-sensing electrically-conductive tissue-contacting plate 912 is shown in cross section and includes a tissue-contacting surface 913. Temperature-sensing electrically-conductive tissue-contacting plate 912 includes a first layer 950 disposed on at least a portion of a bottom surface 919 of an electrically-conductive substrate 911. The first layer 950 includes an electrically-conductive material 981 disposed on an electrically-insulative material 951. An opening 960 is formed in the first layer 950 and configured to receive at least a portion of a temperature sensor 961 therein. In some embodiments, as shown in FIG. 9, a second layer 990 formed of an electrically-insulative material may be configured to cover the temperature sensor 961, the electrically-conductive trace 980, and portions of the first layer 950.

Hereinafter, methods of manufacturing a temperature-sensing electrically-conductive tissue-contacting plate suitable for use in an electrosurgical jaw member are described with reference to FIGS. 10 and 11. It is to be understood that the steps of the methods provided herein may be performed in combination and in a different order than presented herein without departing from the scope of the disclosure.

Figure 10:
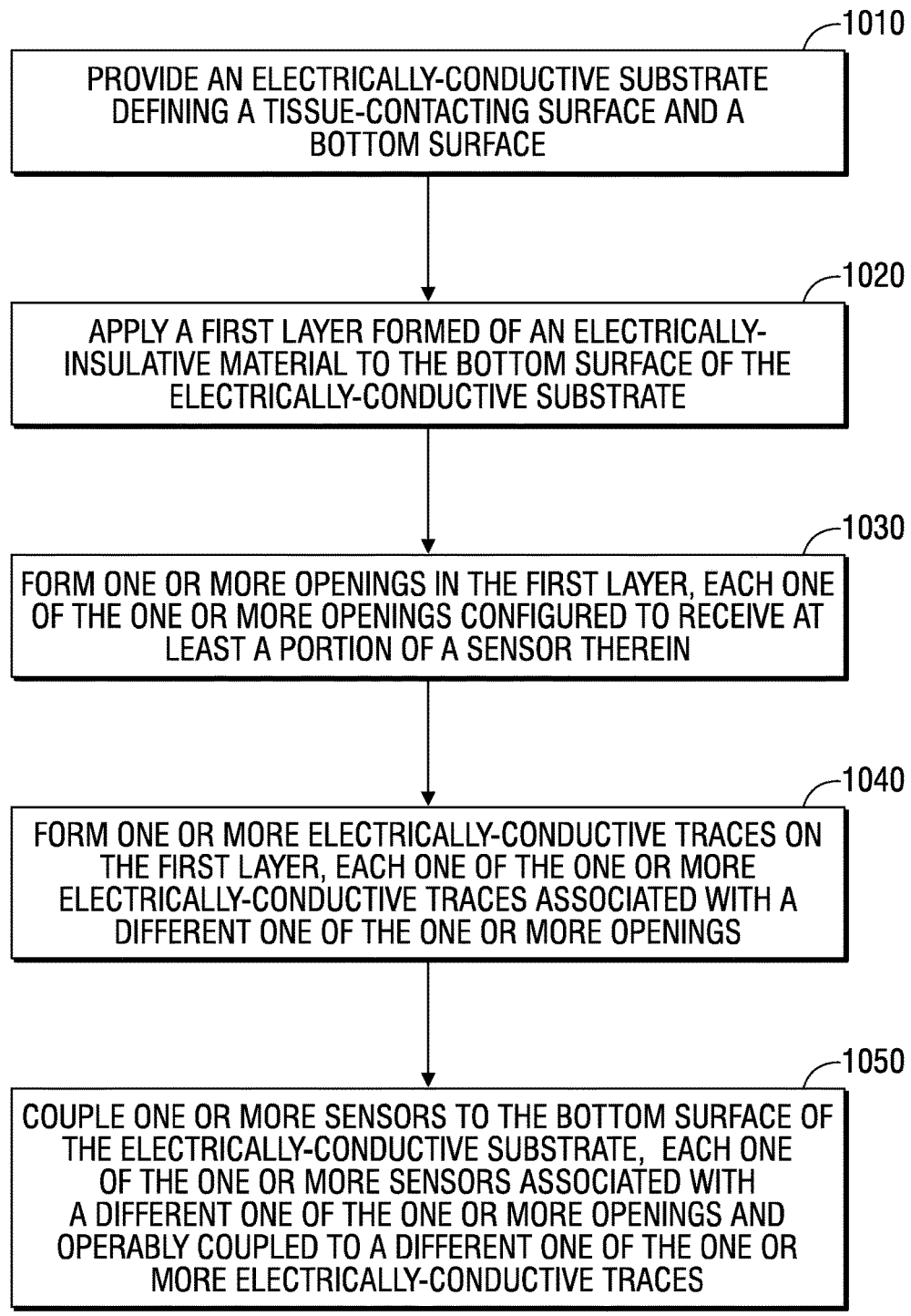
FIG. 10 is a flowchart illustrating a method of manufacturing a temperature-sensing electrically-conductive tissue-contacting plate suitable for use in an electrosurgical jaw member according to an embodiment of the present disclosure.

FIG. 10 is a flowchart illustrating a method of manufacturing a temperature-sensing electrically-conductive tissue-contacting plate suitable for use in an electrosurgical jaw member according to an embodiment of the present disclosure. In step 1010, an electrically-conductive substrate 811 defining a tissue-contacting surface 813 and a bottom surface 819 is provided.

In step 1020, a first layer 850 formed of an electrically-insulative material 851 is applied to the bottom surface 819 of the electrically-conductive substrate 811.

In step 1030, one or more openings 860 are formed in the first layer 850. Each one of the one or more openings 860 is configured to receive at least a portion of a sensor 861 therein. In some embodiments, the sensor 861 is a temperature sensor, e.g., a thermocouple or a thermistor.

In step 1040, one or more electrically-conductive pathways or traces 880 are formed on the first layer 850. Each one of the one or more electrically-conductive traces 880 is associated with a different one of the one or more openings 860.

In step 1050, one or more sensors 861 are coupled to the bottom surface 819 of the electrically-conductive substrate 811. Each one of the one or more sensors 861 is associated with a different one of the one or more openings 860 and operably coupled to a different one of the one or more electrically-conductive traces 880.

Figure 11:
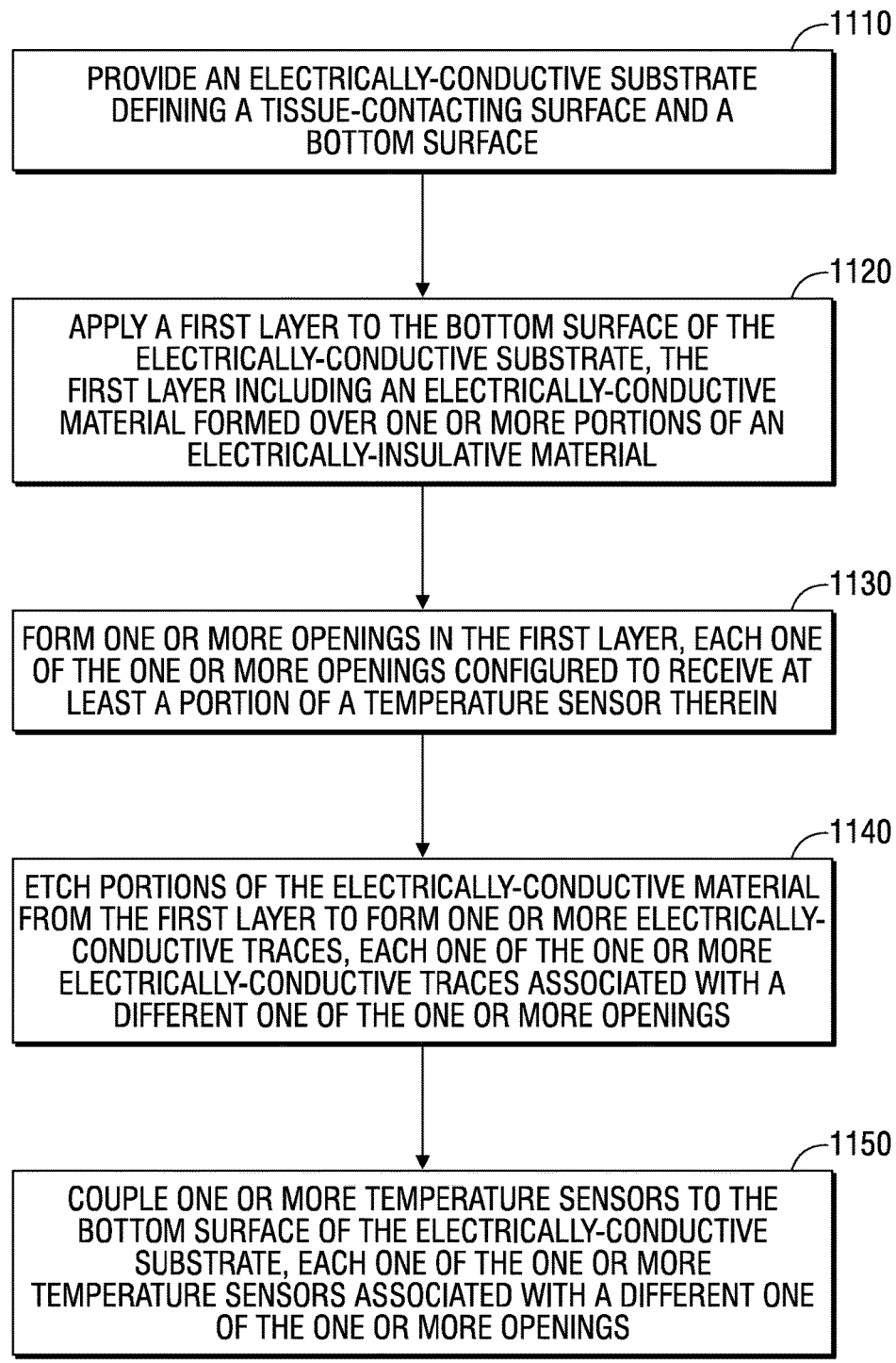
FIG. 11 is a flowchart illustrating a method of manufacturing a temperature-sensing electrically-conductive tissue-contacting plate suitable for use in an electrosurgical jaw member according to another embodiment of the present disclosure.

FIG. 11 is a flowchart illustrating a method of manufacturing a temperature-sensing electrically-conductive tissue-contacting plate suitable for use in an electrosurgical jaw member according to an embodiment of the present disclosure. In step 1110, an electrically-conductive substrate 911 defining a tissue-contacting surface 913 and a bottom surface 919 is provided.

In step 1120, a first layer 950 is applied to the bottom surface 919 of the electrically-conductive substrate 911. The first layer 950 includes an electrically-conductive material 981 formed over one or more portions of an electrically-insulative material 951.

In step 1130, one or more openings 960 are formed in the first layer 950. Each one of the one or more openings 960 is configured to receive at least a portion of a temperature sensor 960 therein.

In step 1140, portions of the electrically-conductive material 981 are etched away from the first layer 950 to form one or more electrically-conductive traces 980. Each one of the one or more electrically-conductive traces 980 is associated with a different one of the one or more openings 960.

In step 1150, one or more temperature sensors (961 are coupled to the bottom surface 919 of the electrically-conductive substrate 911. Each one of the one or more temperature sensors 961 is associated with a different one of the one or more openings 960.

Figure 12:
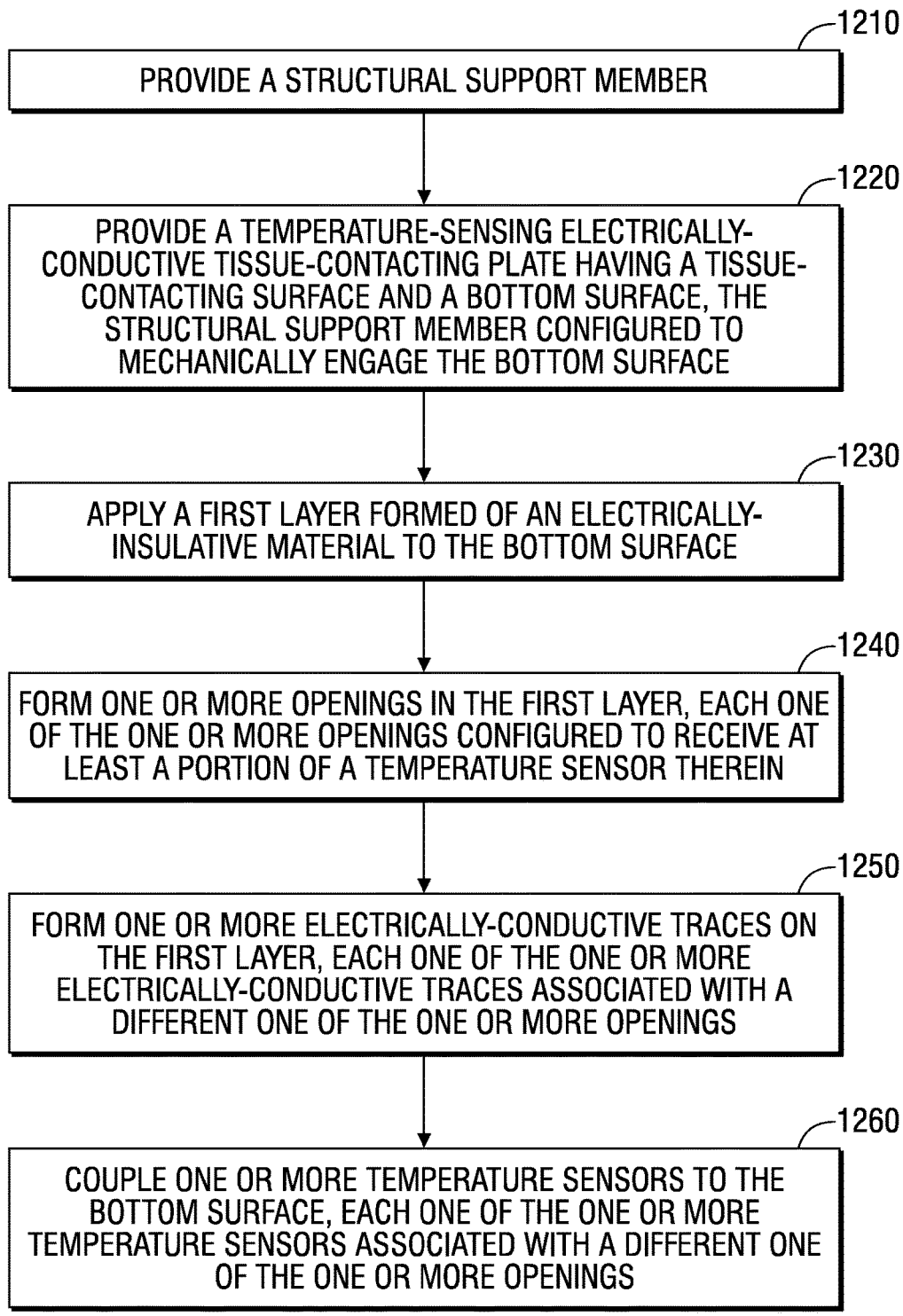
FIG. 12 a flowchart illustrating a method of manufacturing a jaw member suitable for use in an electrosurgical end-effector assembly according to an embodiment of the present disclosure.

FIG. 12 is a flowchart illustrating a method of manufacturing a jaw member suitable for use in an electrosurgical end-effector assembly according to an embodiment of the present disclosure. In step 1210, a structural support member 116 is provided.

In step 1220, a temperature-sensing electrically-conductive tissue-contacting plate 112 having a tissue-contacting surface 113 and a bottom surface 119 is provided. The structural support member 116 is configured to mechanically engage the bottom surface 119.

In step 1230, a first layer 850 formed of an electrically-insulative material 851 is applied to the bottom surface 819.

In step 1240, one or more openings 860 are formed in the first layer 850. Each one of the one or more openings 860 is configured to receive at least a portion of a temperature sensor 861 therein. In some embodiments, the temperature sensor 861 is a thermocouple or a thermistor.

One or more electrically-conductive pathways or traces 880 are formed on the first layer 850. Each one of the one or more electrically-conductive traces 880 is associated with a different one of the one or more openings 860.

In step 1250, one or more temperature sensors 861 are coupled to the bottom surface 819. Each one of the one or more temperature sensors 861 is associated with a different one of the one or more openings 860 and operably coupled to a different one of the one or more electrically-conductive traces 880.

The presently-disclosed jaw members including a temperature-sensing electrically-conductive tissue-contacting plate are capable of directing energy into tissue, and may be suitable for use in a variety of procedures and operations. The above-described bipolar forceps embodiments may utilize both mechanical clamping action and electrical energy to effect hemostasis by heating tissue and blood vessels to coagulate, cauterize, cut and/or seal tissue. The jaw assemblies may be either unilateral or bilateral. The above-described bipolar forceps embodiments may be suitable for utilization with endoscopic surgical procedures and/or open surgical applications.

In the above-described bipolar forceps embodiments, the temperature-sensing electrically-conductive tissue-contacting plates may be used to ensure that tissue has been properly sealed, e.g., by providing a temperature measurement to a controller for use in determining that the tissue has met a minimum threshold temperature for tissue sealing.

The above-described temperature-sensing electrically-conductive tissue-contacting plates may be curved at various angles to facilitate manipulation of tissue and/or to provide enhanced line-of-sight for accessing targeted tissues. In some embodiments, the temperature-sensing electrically-conductive tissue-contacting plate may have a thickness that varies (i.e., non-uniform) from a proximal end to a distal end thereof.

The above-described tissue-contacting plate embodiments may include a plurality of zones, wherein each zone includes one or more sensors, including temperature sensors and/or pressure sensors, e.g., to provide feedback to an electrosurgical power generating source and/or a controller configured to turn on/off different zones to provide more uniform heating patterns across the jaw members and/or to help control thermal spread.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A method of manufacturing a temperature-sensing electrically-conductive tissue-contacting plate suitable for use in an electrosurgical jaw member, comprising:
    providing an electrically-conductive substrate defining a longitudinal axis and having a planar bottom surface;
    applying a first planar layer to the planar bottom surface of the electrically-conductive substrate, the first planar layer including an electrically-conductive material formed over one or more portions of an electrically-insulative material;
    forming a first opening and a second opening in the first planar layer, the first and second openings laterally offset from one another on the planar bottom surface in a direction transverse to the longitudinal axis of the electrically-conductive substrate, each of the first and second openings configured to receive at least a portion of a temperature sensor therein;
    etching portions of the electrically-conductive material from the first planar layer to form a first electrically-conductive trace and a second electrically conductive trace, the first electrically-conductive trace associated with the first opening and the second electrically-conductive trace associated with the second opening; and
    coupling first and second temperature sensors to the planar bottom surface of the electrically-conductive substrate, the first temperature sensor associated with the first opening and the second temperature sensor associated with the second opening.

2. The method of manufacturing a temperature-sensing electrically-conductive tissue-contacting plate of claim 1, wherein at least one of the first or second temperature sensors is a thermocouple.

3. The method of manufacturing a temperature-sensing electrically-conductive tissue-contacting plate claim 2, wherein the thermocouple is a J-type thermocouple formed utilizing vapor deposition.

4. The method of manufacturing a temperature-sensing electrically-conductive tissue-contacting plate of claim 1, wherein at least one of the first or second temperature sensors is a thermistor.

5. The method of manufacturing a temperature-sensing electrically-conductive tissue-contacting plate of claim 1, wherein forming the first and second openings in the first planar layer includes etching at least one of the first or second openings in the first planar layer.

6. The method of manufacturing a temperature-sensing electrically-conductive tissue-contacting plate of claim 1, further comprising:
    forming a third opening in the first planar layer configured to receive at least a portion of a pressure sensor therein; and
    coupling at least two pressure sensors to the bottom planar surface of the electrically-conductive substrate, a first pressure sensor of the at least two pressure sensors associated with the third opening, a second pressure sensor of the at least two pressure sensors associated with the first or second opening.

7. The method of manufacturing a temperature-sensing electrically-conductive tissue-contacting plate of claim 1, wherein providing the electrically-conductive substrate having the planar bottom surface includes the electrically-conductive substrate being rigid.

8. The method of manufacturing a temperature-sensing electrically-conductive tissue-contacting plate of claim 1, wherein etching portions of the electrically-conductive material includes etching the first and second electrically conductive traces parallel to the longitudinal axis of the electrically-conductive substrate.

9. A method of manufacturing a jaw member suitable for use in an electrosurgical end-effector assembly, comprising:
    providing a structural support member;
    providing a temperature-sensing electrically-conductive tissue-contacting plate defining a longitudinal axis and having a tissue-contacting surface and a planar bottom surface, the tissue-contacting plate being solid between the tissue-contacting surface and the bottom surface, the structural support member configured to mechanically engage the bottom surface;
    applying a planar first layer formed of an electrically-insulative material to the bottom surface, the first planar layer including an electrically-conductive material formed over one or more portions of the electrically-insulative material;
    forming a first and second opening in the first layer, the first and second openings each configured to receive at least a portion of a temperature sensor therein, the first and second openings laterally offset from one another in the first layer in a direction transverse to the longitudinal axis;
    etching portions of the electrically-conductive material from the first planar layer to form a first electrically-conductive trace and a second electrically conductive trace, the first electrically-conductive trace associated with the first opening and the second electrically-conductive trace associated with the second opening; and
    coupling a first temperature sensor and a second temperature sensor to the bottom surface, each one of the first and second temperature sensors associated with a different one of the first and second openings and operably coupled to a different one of the first and second electrically-conductive traces.

10. The method of manufacturing a jaw member of claim 9, wherein the at least one of the first or second temperature sensors is a thermocouple including one or more deposited layers formed utilizing vapor deposition.

* * * * *